United States Patent [19]

Miyagawa et al.

[11] Patent Number: 4,854,153
[45] Date of Patent: Aug. 8, 1989

[54] AUTOMATIC CALIBRATION APPARATUS FOR A PARTIAL GAS PRESSURE MEASURING SENSOR

[75] Inventors: Yuichi Miyagawa; Kiwamu Yoneda; Kazuhiro Kuwa; Katsuyuki Kogo, all of Osaka, Japan

[73] Assignee: Sumitomo Electric Industries, Ltd., Osaka, Japan

[21] Appl. No.: 128,402

[22] Filed: Dec. 2, 1987

[30] Foreign Application Priority Data

Dec. 5, 1986 [JP] Japan ................ 61-291356
Dec. 5, 1986 [JP] Japan ................ 61-291357

[51] Int. Cl.⁴ .................................... G01N 27/00
[52] U.S. Cl. ........................................ 73/1 G
[58] Field of Search .............. 73/1 G; 364/571; 340/626, 632, 633

[56] References Cited

U.S. PATENT DOCUMENTS

| | | | |
|---|---|---|---|
| 3,359,784 | 12/1967 | Jorre et al. | 73/1 G |
| 4,100,537 | 7/1978 | Carlson | 340/626 |
| 4,322,964 | 4/1982 | Melgaard et al. | 73/1 G |
| 4,481,804 | 11/1984 | Eberhard et al. | 73/1 G |
| 4,555,930 | 12/1985 | Leach et al. | 73/1 G |
| 4,578,986 | 4/1986 | Navarre | 73/1 G |
| 4,663,958 | 5/1987 | Matthiessen | 73/1 G |
| 4,676,100 | 6/1987 | Eichberger | 73/1 H |

FOREIGN PATENT DOCUMENTS

| | | |
|---|---|---|
| 0074498 | 3/1983 | European Pat. Off. . |
| 2608727 | 9/1977 | Fed. Rep. of Germany . |
| 2645736 | 11/1977 | Fed. Rep. of Germany ....... 73/1 G |
| 57-74651 | 8/1982 | Japan . |
| 0262646 | 11/1986 | Japan ..................... 73/1 G |
| 0645023 | 1/1979 | U.S.S.R. ................ 73/1 G |
| 1470155 | 4/1977 | United Kingdom . |

*Primary Examiner*—Stewart J. Levy
*Assistant Examiner*—Robert R. Raevis
*Attorney, Agent, or Firm*—W. G. Fasse; D. H. Kane, Jr.

[57] ABSTRACT

An automatic calibration apparatus for a partial gas pressure measuring sensor supplies a gas having a high partial pressure (referred to as the high gas) and a gas having a low partial pressure (referred to as the low gas), to a gas selection device (103) from a gas supplier (101) through a detector device (102) which detects an abnormal gas supply condition outside given, satisfactory gas supply conditions. The selection device (103) selects the high gas or the low gas for supplying the selected gas to a sensor support (27 or 104). A partial gas pressure measuring sensor to be calibrated is placed on the sensor support and an automatic calibration controller (106) stores an output of the partial gas pressure measuring sensor (105) in an information storing memory. When the detector device, detects an abnormal gas supply of the high gas or the low gas, the automatic calibration controller stops the storing of the output of the partial gas pressure measuring sensor (105) in the storing means (107).

15 Claims, 9 Drawing Sheets

AUTOMATIC CALIBRATION APPARATUS FOR A PARTIAL GAS PRESSURE MEASURING SENSOR

BACKGROUND OF THE INVENTION

1. Field of the Invention

The present invention relates to an automatic calibration apparatus for a partial gas pressure measuring sensor. More particularly, the present invention relates to an automatic calibration apparatus for a partial gas pressure measuring sensor, in which an output of a transcutaneous partial oxygen pressure measuring sensor or the like is automatically calibrated in atmospheres of at least two kinds of standard gases.

2. Description of the Prior Art

It is a widely utilized method to measure a partial pressure of carbon dioxide gas, oxygen gas or the like in blood by means of an electrochemical sensor such as a transcutaneous oxygen pressure measuring sensor. If such an electrochemical sensor is used to measure a partial gas pressure, the measurement is effected while calibration of the sensor is being done. In the following text an example of measuring a partial pressure of carbon dioxide, referred to hereinafter as $PCO_2$, will be described. $PCO_2$ sensor shows a fixed potential output value representing a corresponding $PCO_2$ value. Therefore, an automatic calibration may be performed by a two-point calibration method using two different standard gases each having a known $PCO_2$ value. Generally two air-mixed gases are used having different carbon dioxide partial gas pressures. The gas having the lower $PCO_2$ value will be referred to as "low gas". The gas having the higher $PCO_2$ value will be called the "high gas" in the following text.

In a conventional automatic calibration apparatus for a $PCO_2$ sensor, it is necessary to avoid a calibration in a state in which the low gas or the high gas is not normally supplied. For this reason, a calibration using the low gas, hereinafter referred to as "low calibration", and a calibration using the high gas, hereinafter referred to as "high calibration", are performed and comparison is made output potentials of the $PCO_2$ sensor are compared with each other. If the difference between those potentials is within a predetermined range, it is determined that the high gas and the low gas are both supplied normally and that the calibrations have been performed normally.

On the other hand, if the potential difference is outside the predetermined range, it is determined that the high gas and the low gas are not supplied normally and that the calibrations are not performed normally. Hence, the calibrations are performed again. Thus, if the high gas and low gas are not normally supplied at the time when the automatic calibration operation is performed, it is necessary to again newly perform both calibrations. The time required for performing the automatic calibration operations is substantial and this undesirable.

SUMMARY OF THE INVENTION

Therefore, it is a primary object of the present invention to provide an automatic calibration apparatus for a partial gas pressure measuring sensor, in which the calibration is immediately stopped when it is determined that one of at least two kinds of standard gases is abnormally supplied, whereby the time required for the automatic calibration can be shortened.

In an automatic calibration apparatus for a partial gas pressure measuring sensor according to another aspect of the present invention, the partial gas pressure measuring sensor is intermittently exposed to a standard gas atmosphere, which makes it possible to improve the measuring precision after the exposure and to also reduce the gas consumption.

Briefly stated, at least two kinds of standard gases are individually supplied to gas selection means from standard gas suppliers through gas supply paths and any one of the at least two kinds of standard gases is selected by the gas selection means to be supplied to a sensor placing means. When the partial gas pressure measuring sensor is placed on the sensor placing means, the sensor is exposed to an atmosphere of the standard gas and an output potential value of the partial gas pressure measuring sensor is stored in storing means. The gas supply paths are provided with detection means for detecting an abnormal supply of the standard gases and when the detection means detects an abnormal supply of any standard gas, the operation for storing the output potential value of the sensor in the storing means is stopped.

Thus, according to the present invention, when an abnormal supply of any of the standard gases is detected, storage of the output potential value of the partial gas pressure measuring sensor in the storing means is immediately stopped and consequently there is no fear of terminating a processing sequence for an automatic calibration without effecting completing a normal calibration.

In a preferred embodiment of the present invention, there is provided a notification means for notifying an abnormal supply of a standard gas when such abnormal supply of the standard gas is detected.

According to a further preferred embodiment of the present invention procedures for performing an automatic calibration are based on the selection of, at least two kinds of standard gases, so that the automatic calibration result corresponds to the selected standard gases.

In a further preferred embodiment of the present invention, a removal of the partial gas pressure measuring sensor from the automatic calibration apparatus is detected and procedures for performing an automatic calibration are changed based on an output of such detection.

In a still further preferred embodiment of the present invention, when the partial gas pressure measuring sensor is placed on the sensor placing means, a time period for supplying a standard gas is being measured and when the measured period attains a prescribed time duration, the supply is stopped. Thus, the standard gas is intermittently supplied by the gas selection means to the sensor placing means, so that the partial gas pressure measuring sensor may be exposed to the atmosphere of a predetermined potential gas pressure.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
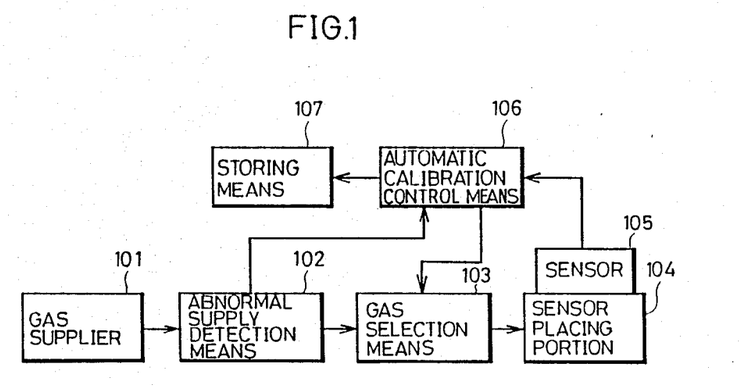
FIG. 1 is a schematic block diagram for explaining a fundamental feature of the present invention.

FIG. 1 is a diagram for explaining an outline of an operation principle of the present invention. A gas supplier 101 supplies the high gas and the low gas. The high gas and the low gas from the gas supplier 101 are supplied to a gas selection means 103 through abnormal gas supply detection means 102. The abnormal gas supply detection means 102 detects abnormal supplies of the low gas and the high gas. The gas selection means 103 selectively supplies the high gas or the low gas to a sensor placing portion 104. The sensor placing portion 104 provides a support for a partial gas pressure sensor 105 to be calibrated. The partial gas pressure sensor 105 is placed on the support to be exposed to an atmosphere of the high gas or the low gas selected by the gas selection means 103, so that an automatic calibration is performed. More specifically, an output potential value of the partial gas pressure sensor 105 is stored in storing means 107 by an automatic calibration control means 106. When an abnormal supply of the high gas or the low gas is detected by the abnormal gas supply detection means 102, the automatic calibration control means 106 stops storing the output potential value of the sensor 105 in the storing means 107.

Figure 2:
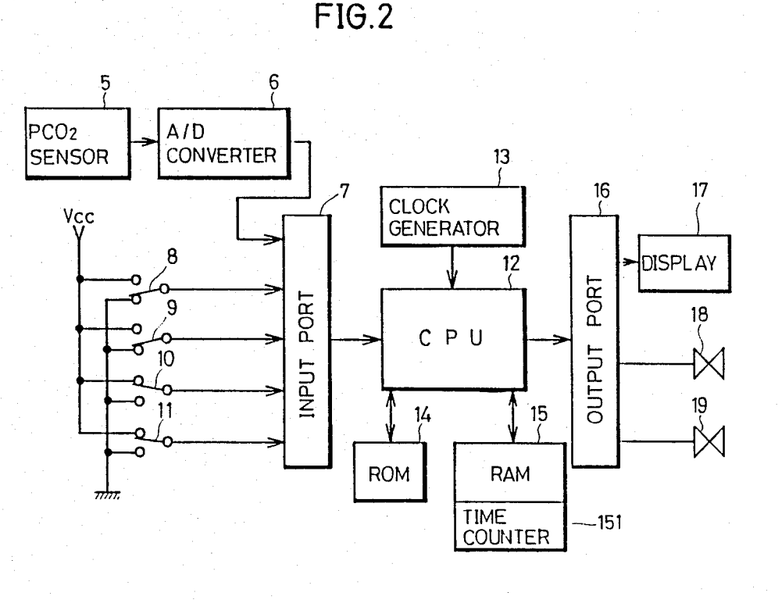
FIG. 2 is a concrete block diagram of a first embodiment of the present invention.
Figure 3:
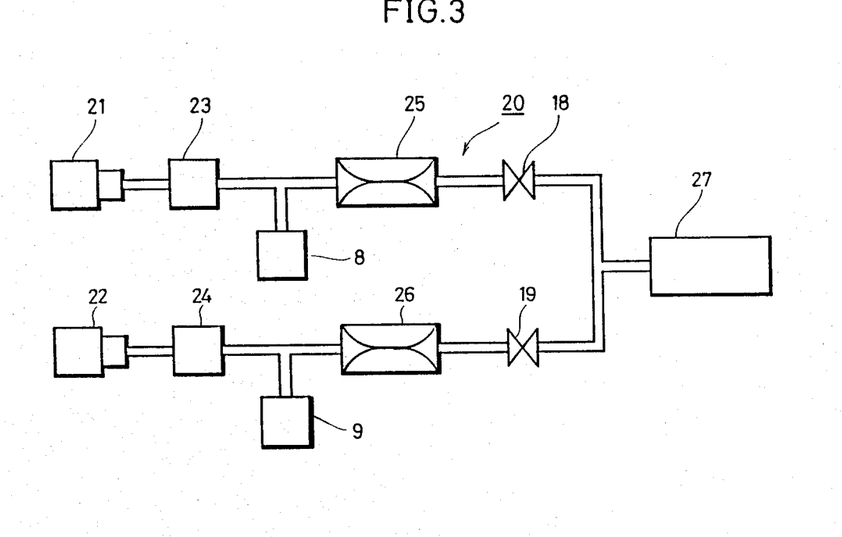
FIG. 3 is an illustration showing gas supply paths for standard gases.
Figure 4:
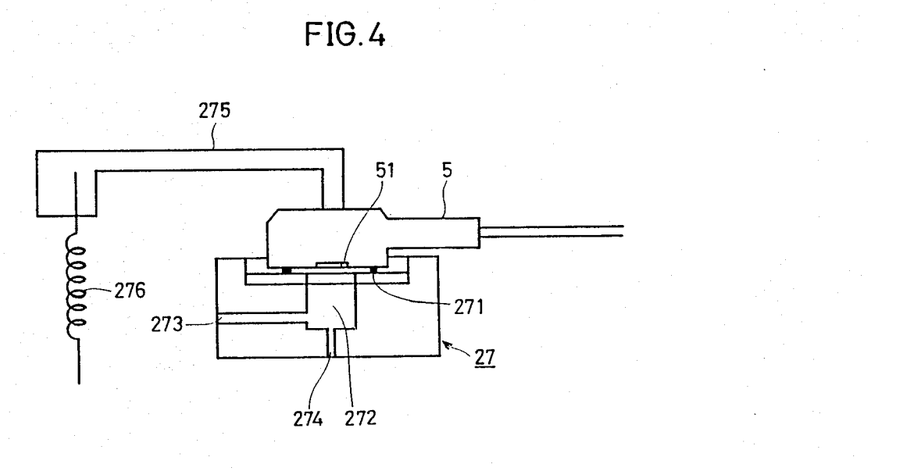
FIG. 4 is an illustration showing a structure of a sensor spot.

Referring to FIGS. 2 to 4, a construction of this embodiment will be described. When a $PCO_2$ sensor 5 is placed on a gas supply support 27, it is exposed to an atomsphere of a standard gas and an output potential of the sensor 5 is supplied to an A/D converter 6, where the output potential is converted to a digital signal. The digital signal is supplied to a central processing unit (CPU) 12 through an input port 7. The input port 7 is connected with a pressure sensitive switch 8 for the detection of an abnormal supply of the low gas, a pressure sensitive switch 9 for the detection of an abnormal supply of the high gas, an automatic calibration switch 10, and an automatic calibration procedure selection switch 11. Contacts of the switches 8 to 11 are connected on one side to a power supply Vcc. The opposite switch contacts are grounded.

The pressure sensitive switch 8 for detecting of an abnormal supply of the low gas and the pressure sensitive switch 9 for detecting an abnormal supply of the high gas are connected to gas supply paths shown in FIG. 3 to be described below. If the switches 8 and 9 are set to the respective contacts on the grounding side, this means that a normal low gas supply and a normal high gas supply are provided. If an abnormal supply of the low gas occurs and a pressure in the gas supply circuit becomes lower than a predetermined value, the pressure sensitive switch 8 for detection of such an abnormal low gas supply is switched over to the power supply Vcc. Similarly, if an abnormal high gas supply occurs, the pressure sensitive switch 9 is switched over to the power supply Vcc. The automatic calibration switch 10 is used to select an execution of an automatic calibration and the automatic calibration procedure selection switch 11 is used to select an execution of a low calibration or a high calibration.

The CPU 12 is connected with the above stated input port 7. Additionally the CPU 12 is also connected with a clock generator 13, an ROM 14, an RAM 15 and an output port 16. A program for controlling the CPU 12 is stored in the ROM 14 prior to operating the system. The CPU 12 performs various operations based on this program. For example, the CPU 12 receives necessary data from the input port 7, communicates data with the RAM 15, determines a time period by counting clock signals supplied by the clock signal generator 13, or outputs necessary data to the output port 16. The RAM 15 is used to store various data and includes a time counter 151 for determining time.

The output port 16 is connected with a display 17 and two-directional electromagnetic valves 18 and 19. The display 17 displays a message indicating an abnormal low gas supply or a normal high gas supply depending on a signal supplied from the output port 16. The two-directional electromagnetic valves 18 and 19 select a high gas supply or a low gas supply depending on an output of the output port 16.

Referring to FIG. 3, a construction of the gas supply paths will be described. A low gas cylinder 21 supplies the low gas and a high gas cylinder 22 supplies the high gas. The low cylinder 21 and the high gas cylinder 22 are connected through pipes to pressure regulators 23 and 24, respectively. The pressure regulators 23 and 24 regulate the pressures of the low gas and of the high gas, respectively, to about 1.5 kg/cm$^2$, for example. Output portions of the pressure regulators 23 and 24 are connected with the pressure sensitive switch 8 for detecting an abnormal low gas supply and the pressure sensitive switch 9 detects an abnormal high gas supply, respectively. Output portions of the switches 8 and 9 are connected through pipes to flow rate regulators 25 and 26, respectively. The flow rate regulators 25 and 26 regulate the flow rates of the low gas and the high gas, respectively, to about 5 ml/min. for example. Outputs of the flow rate regulators 25 and 26 are connected to the above mentioned two-directional electromagnetic valves 18 and 19 shown in FIG. 2, respectively. Output portions of the two-directional electromagnetic valves 18 and 19 are connected to a gas supply support 27 for calibrating the sensor.

The $PCO_2$ sensor 5 is placed on the support 27 for calibration as shown in FIG. 4. More, specifically, the low gas or the high gas introduced through the gas supply paths described above with reference to FIG. 3. The gas inlet path 273 leads to a gas reservoir 272, so that a sensitive surface 51 of the $PCO_2$ sensor 5 is exposed to an atomsphere of the low gas or to an atmosphere of the high gas. A gas outlet path 274 is provided to maintain in the gas reservoir 272 a pressure which is substantially equal to the atmospheric pressure and to permit rapidly replacing the gas in the gas reservoir 272 by another gas. The $PCO_2$ sensor 5 is pressed against a ring-shaped packing or seal 271 by means of a rotating arm 275, so that the gas can be prevented from leaking out between the $PCO_2$ sensor 5 and the support 27.

Figure 5:
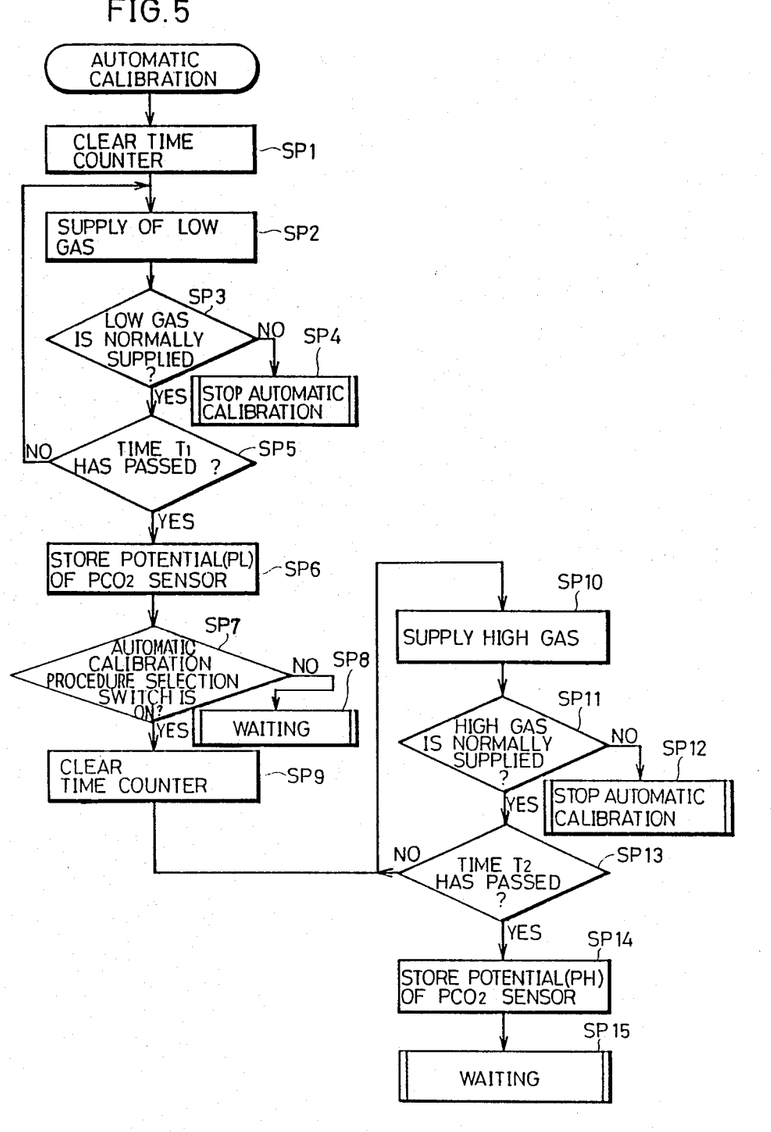
FIG. 5 is a flow chart showing a main routine of the above mentioned first embodiment.

Referring to FIGS. 2 to 8, an actual operation of this embodiment will now be described. First, the $PCO_2$ sensor 5 is placed on the support 27 shown in FIG. 4 and an execution of an automatic calibration is selected by operating the automatic calibration switch 10. Then, a program of the main routine shown in FIG. 5 is started. First in the step SP1, the CPU 12 clears the time counter 151. The time counter 151 is incremented in the interruption processing routine of FIG. 8 executed in response to a clock signal inputted from the clock generator 13 to the CPU 12 with a predetermined cycle. In the step SP2, the CPU 12 opens the two-directional electromagnetic valve 18 for the low gas and closes the two-directional electromagnetic valve 19 for the high gas. As a result, the pressure of the low gas supplied from the low gas cylinder 21 is regulated by the pressure regulator 23 and the flow rate thereof is regulated by the flow rate regulator 25, so that the low gas is supplied to the support 27.

Figure 6:
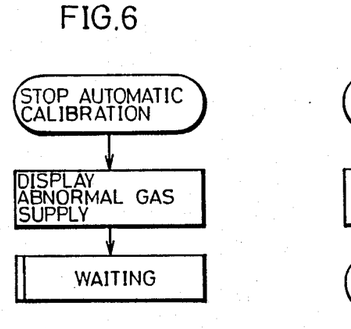
FIG. 6 is a flow chart showing a subroutine for stopping an automatic calibration.

The CPU 12 determines in the step SP3 whether the low gas is normal or not. This determination is effected by reading an output voltage of the pressure sensitive switch 8 through the input port 7. More specifically, if the output voltage of this pressure sensitive switch 8 is OV, it is determined that the low gas supply is normal. If the output voltage is Vcc, it is determined that the low gas supply is not normal so that the CPU 12 proceeds to the step SP4 to stop the processing of the automatic calibration as shown in FIG. 6. Thus, the CPU 12 displays a message on the display 17 indicating that an abnormal low gas supply occurs.

On the other hand, if the low gas supply is normal, the CPU 12 proceeds to step SP5 to determine, based on an output of the time counter 151, whether time T1 has passed or not. If the time T1 has not passed, the CPU 12 repeats the operations in the steps SP2 and SP3 until the output of the time counter 151 indicates a lapse of the time T1. This repetition is required for waiting until the $PCO_2$ sensor 5 on the support 27 is kept in a stable state for sensing the atmosphere of the low gas. If an abnormal low gas supply occurs before the time T1 has passed, the operation for stopping automatic calibration in the step SP4 is executed.

If it it determined in step SP5 based on the output of the time counter 151, that the time T1 has passed, the CPU 12 reads an output potential PL of the $PCO_2$ sensor converted by the A/D converter 6 through the input port 7 and stores it in the RAM 15. The CPU 12 determines in the step SP7 whether execution procedures are selected by the automatic calibration procedure selection switch 11. If the execution procedures are not selected by the automatic calibration procedure selection switch 11, the CPU 12 proceeds to the step SP8 to execute the routine for waiting shown in FIG. 7.

More specifically, the CPU 12 closes the two-directional electromagnetic valves 18 and 19 in step SP81 to stop the gas supply and clears the time counter 151 in step SP82. Then, in step SP83, the CPU 12 determines whether the automatic calibration switch 10 is turned on or not. If it is not turned on, the automatic calibration is brought to an end in step SP84. If the automatic calibration switch 10 is turned on, it is determined in step SP85 whether the output of the time counter 151 indicates a lapse of time T3 or not. If the time T3 has not passed, the operations in steps SP83 and SP85 are repeated. If it is determined that the time T3 has passed, the CPU 12 returns again to the main routine shown in FIG. 5.

If it is determined in step SP7 that the execution procedures are selected by the automatic calibration procedure selection switch 11, the CPU 12 clears the time counter 151 in step SP9. Then, in step SP10, the CPU 12 closes the two-directional electromagnetic valve 18 for the low gas and opens the two-directional electromagnetic valve 19 for the high gas, for supplying high gas to the sensor support 27. Thus, a pressure of the high gas from the high gas cylinder 22 is regulated by the pressure regulator 24 and the flow rate of the high gas is regulated by the flow rate regulator 26. CPU 12 determines in the step SP11 whether the high gas supply is normal or not.

If the high gas supply is not normal, the CPU 12 stops the automatic calibration in step SP12 and displays a message on the display 17 indicating an abnormal high gas supply. If the high gas supply is normal the CPU 12 determines in step SP13 whether a time T2 has passed or not, based on an output of the time counter 151. If the time T2 has not passed, the operations in the steps SP10 and SP11 are repeated. If the time T2 has passed, the CPU 12 reads an output potential PH of the $PCO_2$ sensor 5 converted as a digital signal by the A/D converter 6 through the input port 7 and stores the output potential PH in the RAM8. Then, the CPU 12 executes the processing routine for waiting shown in FIG. 7.

Now, procedures to be executed on the occurrence of an abnormal low gas supply or an abnormal high gas supply will be described. When an abnormal low gas supply or an abnormal high gas supply is detected, a respective message is displayed on the display portion 17 and accordingly when the user confirms the message, he terminates the automatic calibration by operating the automatic calibration switch 10. Then, the user executes recovery procedures such as replacement of the low gas cylinder 21 or the high gas cylinder 22 and selects again an execution of an automatic calibration by using the automatic calibration switch 10 to restart the automatic calibration program shown in FIG. 5.

Figure 9A:
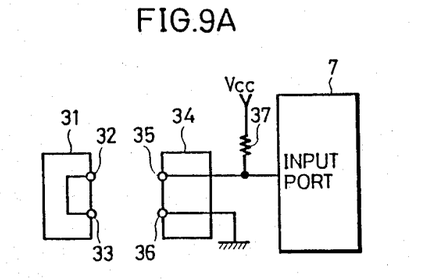
FIGS. 9A and 9B are diagrams showing a connection portion of a $PCO_2$ sensor in a second embodiment of the present invention.
Figure 9B:
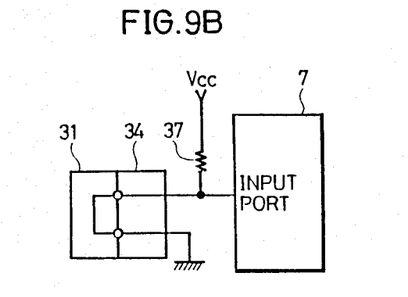

FIGS. 9A and 9B are diagrams showing the connection between the $PCO_2$ sensor and the automatic calibration apparatus in a second embodiment of the present invention. Particularly, FIG. 9A shows a state in which the $PCO_2$ sensor is not connected and FIG. 9B shows a state in which the $PCO_2$ sensor is connected.

In FIGS. 9A and 9B, a connector 31 is provided in the $PCO_2$ sensor with terminals 32 and 33 which are short-circuited. A connector 34 is provided in the automatic calibration apparatus and has a terminal 35 connected to the input port 7 and to a DC power supply Vcc through a pull-up resistor 37 with a grounded terminal 36. Accordingly, if the $PCO_2$ sensor 5 shown in FIG. 2 is not connected to the apparatus, a voltage Vcc is applied to the input port 7. On the other hand, if the PCO₂ sensor 5 is connected to the apparatus, a voltage OV is applied to the input port 7 since the terminals 32 and 33 of the connector 31 in the PCO₂ sensor 5 are connected to the terminals 35 and 36 of the connector 34 in the apparatus, respectively.

Figure 10:
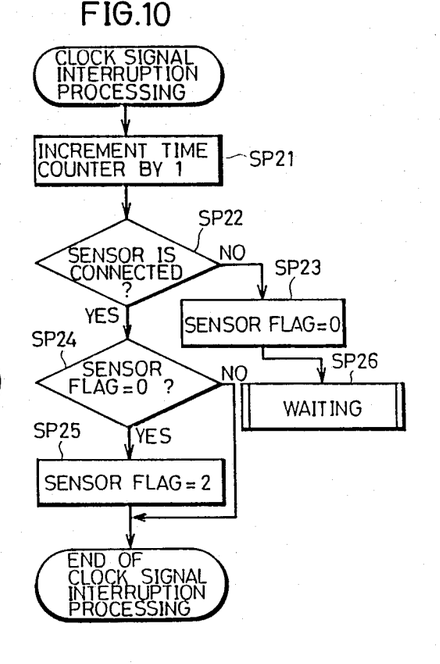
FIG. 10 is a flow chart showing a clock signal interruption processing routine in the second embodiment.
Figure 11:
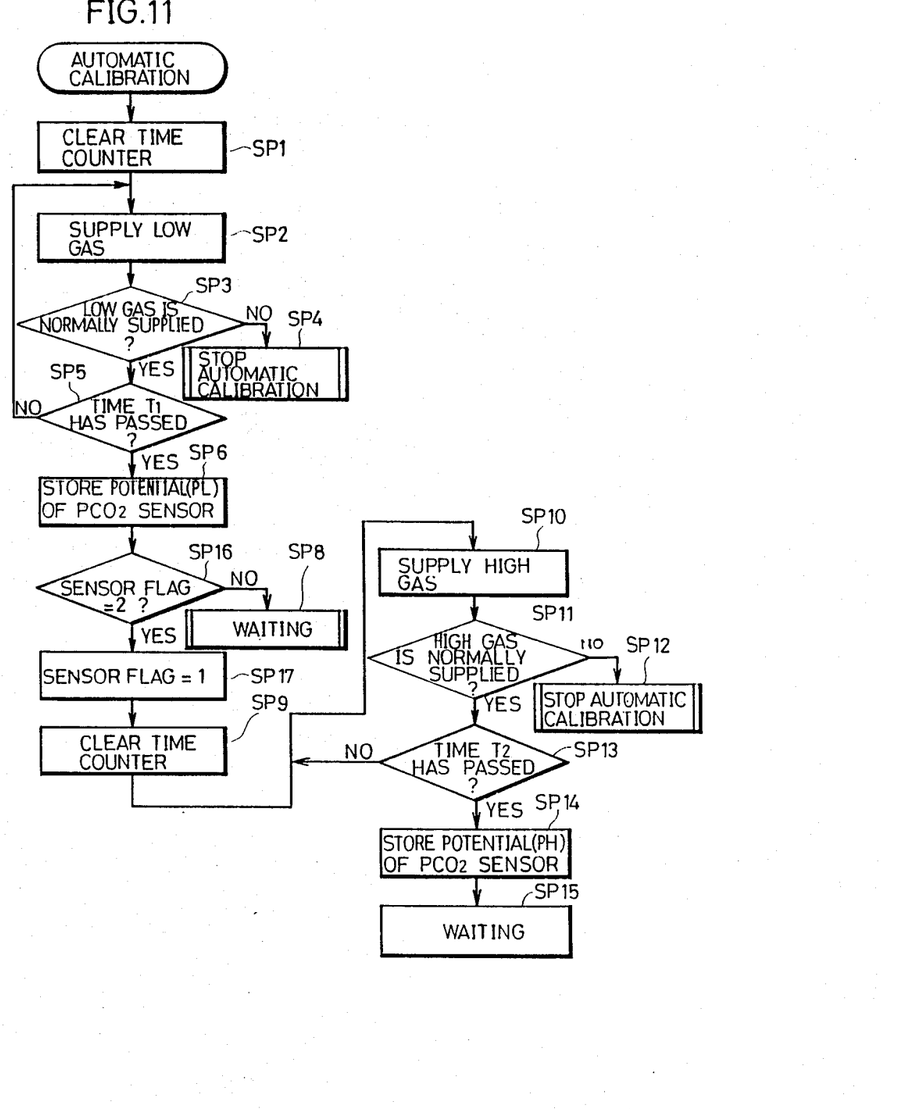
FIG. 11 is a flow chart showing a main routine of the second embodiment.

FIG. 10 shows a clock signal interruption processing routine in the second embodiment, and FIG. 11 shows a main routine in this embodiment.

An actual operation of this embodiment will now be described in the following. When a clock signal is supplied from the clock signal generator 13 to the CPU 12, a program executed at that time is temporarily suspended, and the CPU 12 interrupts the clock signal processing routine shown in FIG. 10. Then, in step SP21, the CPU 12 increments the time counter 151 by 1 and determines in step SP22 whether the PCO₂ sensor 5 is connected to the automatic calibration apparatus or not. This determination is effected by reading a voltage inputted from the connector 34 to the input port 7. More specifically, if the voltage inputted to the input port 7 is the power supply voltage Vcc, the CPU 12 determines that the PCO₂ sensor 5 is not connected. If it is OV, the CPU 12 determines that the PCO₂ sensor 5 is connected.

Figure 7:
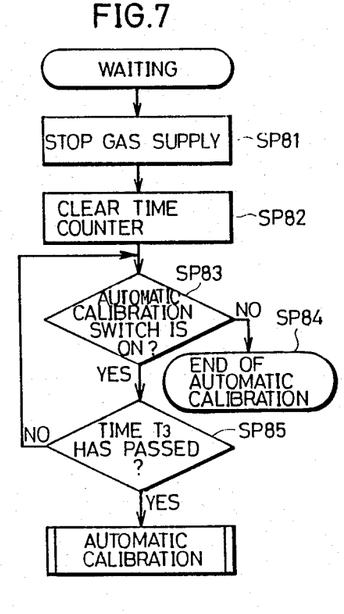
FIG. 7 is a flow chart showing a subroutine for waiting.
Figure 8:
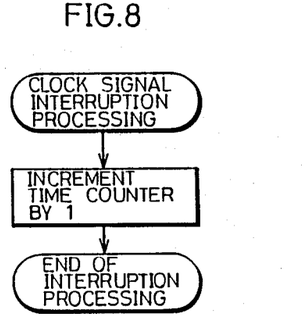
FIG. 8 is a flow chart showing a clock signal interruption processing routine.

If the PCO₂ sensor 5 is not connected, a sensor flag stored in the RAM 15 is reset to 0 in step SP23, so that the CPU 12 proceeds to step SP26 to execute the routine for waiting shown in FIG. 7. On the other hand, if it is determined that the PCO₂ sensor 5 is connected, the CPU 12 determines in step SP24 whether the sensor flag is 0 or not. If the sensor flag is 0, a value of the sensor flag is set to 2, so that execution of the clock signal interruption processing routine is brought to an end to restart execution of the suspended program. The value of the sensor flag is a variable indicating a state of connection of the PCO₂ sensor 5. The flag "0" represents a state in which the PCO₂ is not connected, while the flags "1" and "2" both represent a state in which the PCO₂ sensor 5 is connected. Particularly, the flag "2" represents a state in which the PCO₂ sensor 5 is not connected but changes its state to be connected, while an automatic calibration is not executed yet. The flag "1" represents the other states.

Referring to FIG. 11, the main routine will now be described. The steps SP1 to SP6 in FIG. 11 are the same as in FIG. 5 and therefore description thereof is omitted. CPU 12 determines in the step SP16 whether the sensor flag is "2" or not. If the sensor flag is not "2", the CPU 12 proceed to step SP8 to execute the subroutine for waiting. On the other hand, if the sensor flag is "2", the sensor flag is set to "1" in step SP17 and then in the same manner as described above in connection with FIG. 5, the operations of steps SP9 to SP15 are executed. More specifically, in this second embodiment, when the CPU 12 determines that the PCO₂ sensor 5 is replaced by a new one, which is newly connected, it automatically selects and executes procedures for an automatic calibration.

As described above, in this second embodiment, the two-point calibration operation including the low calibration and the high calibration is, executed only when both the low calibration and the high calibration are required, for example, in case in which the presently connected PCO₂ sensor 5 is replaced by a new one. In other cases, it becomes possible to perform only the one-point calibration, i.e., either the low calibration or the high calibration. As a result, a period of time required for executing an automatic calibration can be shortened.

Although the invention is applied to the automatic calibration apparatus for the PCO₂ sensor 5 in the above described embodiments, the present invention is not limited thereto. The invention is applicable to transcutaneous oxygen partial pressure sensors, to combined sensors which transcutaneously measure the partial oxygen pressure and the partial carbon dioxide pressure, or the like.

Thus, according to the above described embodiments of the present invention, while any of two or more kinds of standard gases is supplied to the sensor support 27 where the partial pressure measuring sensor is exposed to a standard gas atmosphere, automatic calibration is stopped upon detection of an abnormal supply of the standard gas. Consequently, it becomes possible to eliminate the disadvantage of the conventional apparatus that an abnormal supply of the standard gas cannot be detected without an automatic calibration by the two-point calibration method using two kinds of standard gases. Thus, the period of time required for execution of automatic calibration can be reduced.

Figure 12:
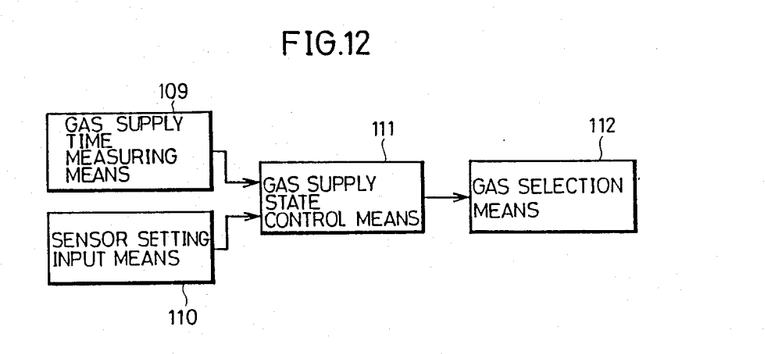
FIG. 12 is a block diagram for explaining an outline of a third embodiment of the present invention.

FIG. 12 is a diagram for explaining an outline of a third embodiment of the present invention, wherein gas supply time measuring means 109 measures the time for supplying the high gas or the low gas, and a sensor setting input means 110 inputs a signal indicating that the above stated PCO₂ sensor 105 is placed on the sensor support 104. A gas selection means 112 is driven by a gas supply state control means 111, whereby the PCO₂ sensor 105 is intermittently exposed to an atmosphere of the low gas or of the high gas if the PCO₂ sensor 105 is placed on the sensor support 104 but a calibration is not yet performed.

Figure 13:
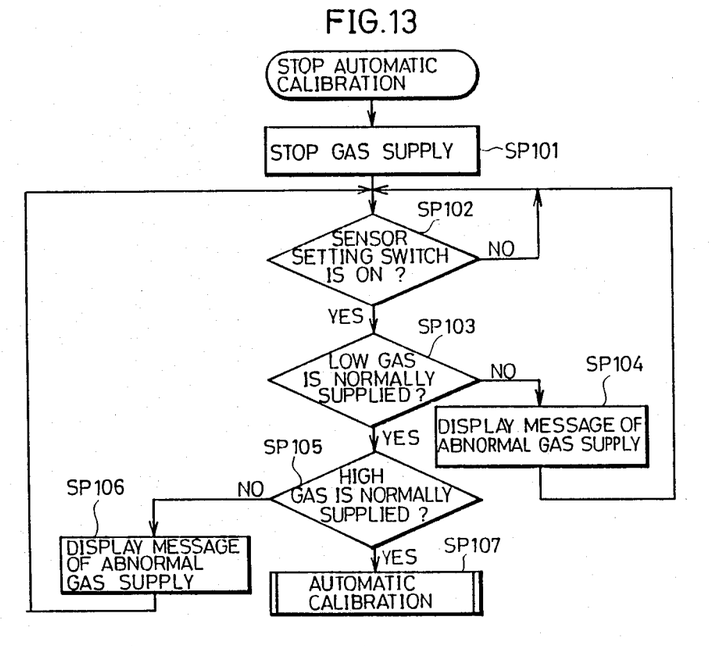
FIG. 13 is flow chart showing a subroutine for stopping an automatic calibration in the third embodiment.

The automatic calibration apparatus in this third embodiment is constructed in the same manner as shown in FIGS. 2 to 4. The automatic calibration routine of this embodiment is the same as described above in connection with FIG. 5. Therefore, detailed description thereof is omitted. First, when the power supply is turned on, the automatic calibration stop program shown in FIG. 13 is started. More specifically, the CPU 12 supplies signals to the two-directional electromagnetic valves 18 and 19 through the output port 16 in step SP101, thereby to close the two-directional electromagnetic valves 18 and 19. Subsequently, in step SP102, the CPU 12 reads a state of the sensor setting switch 10 through the input port 7 and determines whether the sensor setting on the sensor support 104 is selected or not. This determination is repeated until the user sets the PCO₂ sensor 5 on the sensor support 104 and selects an execution of an automatic calibration by using the sensor setting switch 10.

If the sensor setting on the sensor support 104 is selected, the CPU 12 determines in step SP103 whether the low gas supply is normal or not and determines in step SP105 whether the high gas supply is normal or not. These determinations are effected by reading the states of the pressure sensitive switches 8 and 9 for detection of abnormal supply of the high gas "through", the input port 7. More specifically, if the output voltages of the pressure sensitive switch 8 for detecting of an abnormal supply of the low gas and the pressure sensitive switch 9 for detecting of an abnormal supply of the high gas are identical to the potential of the power supply Vcc, it is determined that an abnormal supply occurs. If each of the output voltages is OV, it is determined that each supply is normal.

If the CPU 12 determines that the low gas supply is not normal, it displays in step SP104 a message in the display 17 representing an abnormal low gas supply. If the CPU 12 determines that the high gas supply is not normal, it displays in step SP106 a message in the display 17 representing an abnormal high gas supply. On the other hand, if it is determined in steps SP103 and SP105 that the low gas supply and the high gas are both normal, it executes, in step SP107, automatic calibration as described above in connection with FIG. 5.

Figure 14:
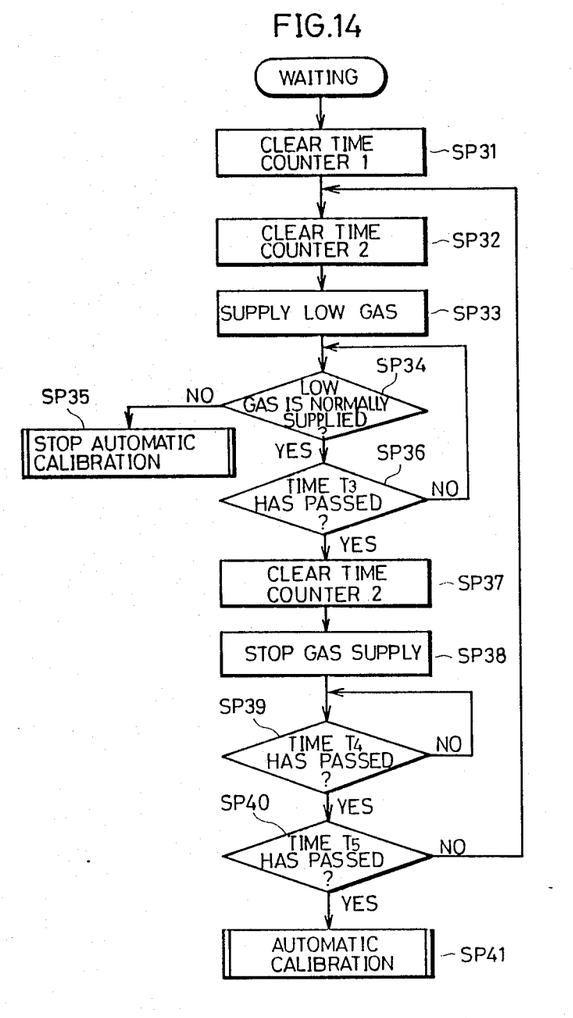
FIG. 14 is a flow chart showing a subroutine for waiting in the third embodiment.

Referring now to FIG. 14, an example of the waiting routine in this embodiment will be described. In a waiting operation, the CPU 12 clears a first time counter 1 in step SP31 and clears a further time counter 2 in step SP32. These time counters are embodied in the time counter 151. The value of the time counter 2 is a variable having the same function as that of the time counter 1 and is stored in the RAM 15 by a program. Then, the CPU 12 opens the two-directional electromagnetic valve 18 in step SP33 to start the low gas supply and determines in step SP34 whether the low gas supply is normal or not. Then, in step SP36, it is determined based on the value of the time counter 2 whether the time T3 has passed after the start of the low gas supply. If the time T3 has not passed, the operations of steps of SP34 and SP36 are repeated. If an abnormal low gas supply occurs before the lapse of the time T3, the automatic calibration stop program shown in FIG. 13 is executed. On the other hand, if it is determined in step SP36 that the time T3 has passed, the CPU 12 clears the time counter 2 in step SP37 and closes the two dimensional electromagnetic valve 18 in step SP38 to stop the low gas supply.

Further in the step SP39, the CPU 12 determines whether the time counter 2 has measured time T4 or not and if not, it waits for the time T4 to lapse. When the CPU 12 determines in step SP39 that the time counter 2 has measured the time T4, it determines in step SP40 whether the time counter 1 has measured time T5 or not. If the time T5 has not passed, the CPU 12 returns to the above stated step SP32 and repeats the operations in steps SP32 to SP40 until the time T5 has passed. When it is determined based on the value of the time counter 1 that the time T5 has passed, the CPU 12 executes the automatic calibration program in step SP41.

Figure 15:
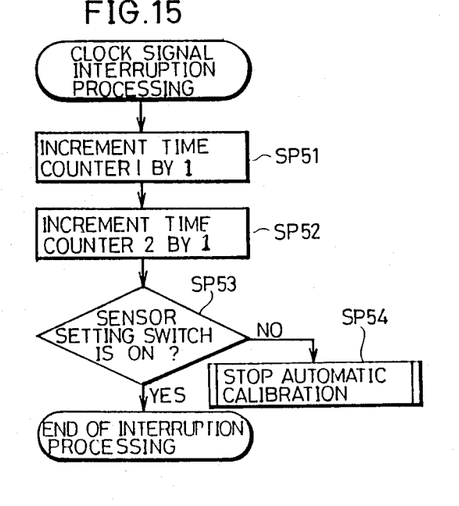
FIG. 15 is a flow chart showing a clock signal interruption processing routine in the third embodiment.

Referring now to FIG. 15, an example of the clock signal interruption processing routine in this embodiment will be described. In this example, when a clock signal is inputted from the clock generator 13 to the CPU 12, a program executed at that time is temporarily suspended and the clock signal interruption processing routine is executed. When the execution of this routine is completed, execution of the suspended program is continued. The CPU 12 increments in steps SP51 and SP52 the variable values of both time counters 1 and 2 by "one". These incremented values are stored in the RAM 15, respectively. Then in step SP53, the CPU 12 determines whether the sensor setting switch 10 is turned on or not. If the sensor setting switch 10 is turned on, the interruption processing is brought to an end to restart the execution of the suspended program. On the other hand, if the sensor switch 10 is turned off, the CPU 12 proceeds to step SP54 without restarting execution of the suspended program, so as to execute the automatic calibration stop program shown in FIG. 13.

Figure 16:
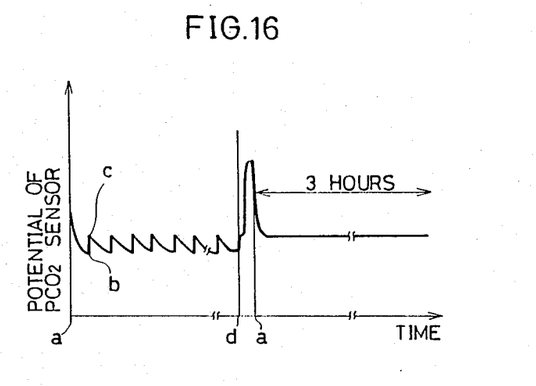
FIGS. 16 to 18 are graphs showing changes in potential of a $PCO_2$ sensor in the third embodiment.
Figure 17:
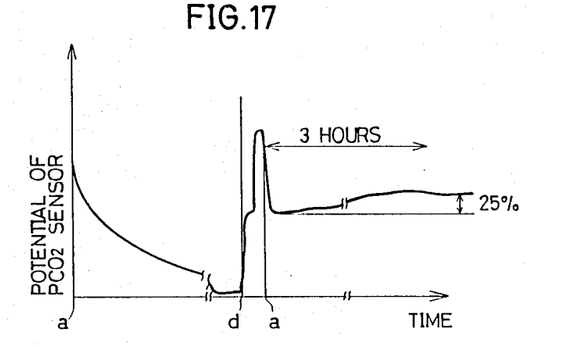
Figure 18:
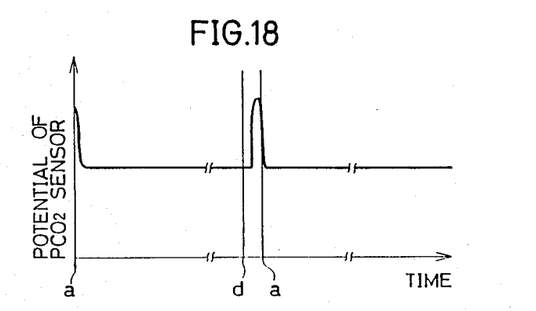

FIGS. 16 to 18 are graphs showing potential changes of the PCO$_2$ sensor in the third embodiment.

In FIG. 16, the point "a" represents the time of an end of the automatic calibration operation, and after that, a waiting operation starts. The point "b" represents the starting time of the low gas supply in a waiting state; the point c represents the stopping time of the low gas supply; and the point "d" represents the starting time of the second automatic calibration operation. After the second automatic calibration operation is terminated, the PCO$_2$ sensor 5 is exposed to the atmosphere of the low gas so that a measuring experiment is conducted.

FIG. 17 shows a potential change of the PCO$_2$ sensor 5 in the case in which the low gas is not supplied in the waiting state after the end of the first automatic calibration. In the same manner as in the case of FIG. 16, the PCO$_2$ sensor 5 is exposed to the atmosphere of the low gas after the end of the second automatic calibration.

FIG. 18 shows a potential change of the PCO$_2$ sensor 5 in the case in which the low gas is continuously supplied in the waiting state after the end of the first automatic calibration. In this case also, the PCO$_2$ sensor 5 is exposed to the atmosphere of the low gas after the end of the second automatic calibration in the same manner as in the cases in FIGS. 16 and 17.

Comparing the case of FIG. 16 with the case of FIG. 17, the time required for establishing a stable state of the PCO$_2$ sensor 5 in the second calibration is shorter in the case of FIG. 16 than that in the case of FIG. 17. In addition, as to the result of the measuring experiment conducted after the end of the second calibration, in the case of FIG. 17, there was an initial drift of 25% for three hours after the start of the measurement of the experiment, while there was little drift in the case of FIG. 16 and in the case of FIG. 18. Furthermore, in the case of FIG. 16, a ratio between the low gas supply time and the gas supply stop time is in a range from 1:30 to 1:40 and the low gas consumption in the waiting state is 1/30 to 1/40 of that in the case of FIG. 18.

Although the invention is applied to the PCO$_2$ sensor also in the above described third embodiment, the present invention is not limited thereto and the invention is applicable to a transcutaneous oxygen partial pressure sensor, a combined sensor which transcutaneously measures partial oxygen pressure and a partial carbon dioxide pressure, or the like.

Thus, according to the third embodiment of the present invention, the partial gas pressure measuring sensor placed on the sensor support is intermittently exposed to the atomsphere of the standard gas at predetermined time intervals. Consequently, the measurement precision after that can be improved and the gas consumption can be reduced.

Although the present invention has been described and illustrate in detail, it is clearly understood that the same is by way of illustration and example only and is not to be taken by way of limitation, the spirit and scope of the present invention being limited only by the terms of the appended claims.

What is claimed is:

1. An automatic calibration apparatus for a partial gas pressure measuring sensor, for calibrating said sensor in atmospheres of at least two kinds of standard gases, comprising standard gas suppliers for supplying said at least two kinds of standard gases, sensor support means on which said partial gas pressure measuring sensor to be calibrated is placed, for exposing said sensor to the atmospheres of said standard gases, gas supply path means for individually introducing said at least two kinds of standard gases from said standard gas suppliers to said sensor support means, detection means coupled to said gas supply path means for detecting an abnormal supply of said standard gases, gas selection means connected to said gas supply path means for selecting any one of said at least two kinds of standard gases to be supplied from said standard gas suppliers and supplying the selected gas to said sensor support means, storing means for storing an output of said partial gas pressure measuring sensor, and control means for normally storing the output of said partial gas pressure measuring sensor in said storing means when the partial gas measuring sensor placed on said sensor support means, is exposed to the atmospheres of the standard gases, said control means stopping the storage of the output of said partial gas pressure measuring sensor in said storing means when said detection means detects that the supply of the standard gases does not meet set conditions thereby indicating said abnormal supply.

2. The automatic calibration apparatus for a partial gas pressure measuring sensor in accordance with claim 1, further comprising procedure selection instructing means for issuing an instruction for selecting procedures of execution of an automatic calibration of said sensor, said control means comprising automatic calibration executing means responsive to an instruction from said procedure selection instructing means for enabling said gas selection means to select any of said at least two kinds of standard gases and executing an automatic calibration corresponding to the selected standard gas.

3. The automatic calibration apparatus for a partial gas pressure measuring sensor in accordance with claim 2, further comprising
connection means for connecting said partial gas pressure measuring sensor to said control means in a removable manner,
said control means comprising means for changing procedures of execution of an automatic calibration in response to a determination that said partial gas pressure measuring sensor is removed from said control means by said connection means.

4. The automatic calibration apparatus for a partial gas pressure measuring sensor in accordance with claim 1, further comprising
automatic calibration instructing means for issuing an instruction to execute an automatic calibration of said sensor,
said control means comprising means for storing the output of said partial gas pressure measuring sensor in said storing means in response to the instruction from said automatic calibration instructing means.

5. The automatic calibration apparatus for a partial gas pressure measuring sensor in accordance with claim 1, further comprising
time measuring means for measuring a period of supply of the standard gas selected by said gas selection means,
said control means comprising means for switching said selection means to supply any of said at least two kinds of standard gases to said sensor support means each time said time measuring means has measured a predetermined period.

6. The automatic calibration apparatus for a partial gas pressure measuring sensor in accordance with claim 1, further comprising means for issuing an indication when said detection means detects that the supply of any of the standard gases does not meet set conditions.

7. The automatic calibration apparatus for a partial gas pressure measuring sensor in accordance with claim 1, wherein
said standard gas suppliers comprise gas cylinders provided corresponding to the respective ones of said at least two kinds of standard gases,
said gas selection means comprises valve members provided corresponding to the respective gas cylinders, and
said gas supply path comprises means for connecting said gas cylinders to said valve members and connecting output portions of said valve members to said sensor support means.

8. The automatic calibration apparatus for a partial gas pressure measuring sensor in accordance with claim 7, wherein
said detection means comprise pressure detecting means connected between said gas cylinders and said valve members for detecting pressures of said at least two kinds of standard gases.

9. The automatic calibration apparatus for a partial gas pressure measuring sensor in accordance with claim 7, further comprising
pressure regulating means connected between said gas cylinders and said valve members for regulating pressures of said at least two kinds of standard gases.

10. The automatic calibration apparatus for a partial gas pressure measuring sensor in accordance with claim 7, further comprising
flow rate regulating means connected between said gas cylinders and said valve members for regulating flow rates of said at least two kinds of standard gases.

11. The automatic calibration apparatus for a partial gas pressure measuring sensor in accordance with claim 7, wherein
said gas cylinders comprise cylinders for supplying standard gases having different gas partial pressures.

12. The automatic calibration apparatus for a partial gas pressure measuring sensor in accordance with claim 1, wherein
said partial gas pressure measuring sensor comprises any of a sensor for transcutaneously measuring partial pressure of oxygen, a sensor for transcutaneously measuring partial pressure of carbon dioxide gas, and a combined sensor for transcutaneously measuring partial pressure of oxygen and partial pressure of carbon dioxide.

13. An automatic calibration method for a partial gas pressure measuring sensor, for calibrating said sensor in atmospheres of at least two kinds of standard gases, comprising the steps of: placing said partial gas pressure measuring sensor on sensor support means, supplying any one of said at least two kinds of standard gases to said sensor placing means to expose said sensor to the atmosphere of the supplied standard gas, storing an output of said partial gas pressure measuring sensor placed in the atmosphere of said standard gas, detecting a state of supply of said standard gas, stopping the storage of the output of said partial gas pressure measuring sensor upon detection of an abnormal gas supply condition which is outside of given gas supply conditions for the supply of said standard gas, and notifying the presence of a detected abnormal gas supply condition.

14. An automatic calibration apparatus for a partial gas pressure measuring sensor, for calibrating said sensor in atmospheres of at least two kinds of standard gases, comprising standard gas suppliers for supplying said at least two kinds of standard gases, sensor support means on which said sensor to be calibrated is placed for a calibration procedure, said sensor support means comprising a gas reservoir for storing said standard gases and exposing a sensitive surface of said sensor to the atmosphere of said standard gases, a gas inlet path for supplying said standard gases to said gas reservoir, a gas outlet path for maintaining pressure in said gas reservoir to be substantially equal to an atmospheric pressure and for rapidly performing the gas replacement, said sensor support means further including seal means for keeping an airtight seal between said sensor and said gas reservoir, gas supply path means for intermittently introducing said standard gases from said standard gas suppliers into said gas reservoir of said sensor means, gas selection means connected to said gas supply path means for selecting any of said at least two kinds of standard gases to supply the selected gas to said gas supply path means, time measuring means for measuring predetermined time intervals of supply of the standard gas selected by said gas selection means, input means for inputting an information that said partial gas pressure measuring sensor is placed on said sensor support means, control means connected to said gas selection means for determining whether a calibration is to be performed, said control means further determining, while a calibration is not being performed, whether one of said standard gases is being supplied and if so, which of said standard gases is being supplied each time said time measuring means has measured a predetermined time interval in response to the input of said input means, for intermittently exposing said partial gas pressure measuring sensor to a predetermined gas atmosphere, thereby to control said gas selection means for intermittently supplying the determined standard gas to said gas reservoir of said sensor support means, whereby the measuring precision is improved and the consumption of standard gas reduced.

15. An automatic calibration method for a partial gas pressure measuring sensor, for calibrating said sensor in atmospheres of at least two kinds of standard gases, comprising the steps of: placing said partial gas pressure measuring sensor to be calibrated on sensor support means, supplying any one of said at least two kinds of standard gases to said sensor support means to expose said sensor to the atmosphere of the supplied standard gas, inputting an input signal signifying that said partial gas pressure measuring sensor is placed on said sensor support means, determining whether a calibration is performed in response to said input signal, and measuring, while a calibration is not being performed, an intermittent supply time interval of said standard gases, determining the standard gas to be supplied each time a predetermined time interval has been measured, and intermittently performing said supplying of the determined standard gas into a reservoir in said sensor support means in accordance with said intermittent supply time interval for improving the measuring precision and reducing the consumption of standard gas.

* * * * *